United States Patent [19]
Sekiya et al.

[11] Patent Number: 5,864,361
[45] Date of Patent: Jan. 26, 1999

[54] VIDEO ENDOSCOPE SYSTEM WITH COLOR TONE CORRECTION

[75] Inventors: Takaomi Sekiya; Tomohiko Kanzaki, both of Tokyo, Japan

[73] Assignee: Asahi Kogaku Kogyo Kabushiki Kaisha, Tokyo, Japan

[21] Appl. No.: 827,710

[22] Filed: Apr. 8, 1997

Related U.S. Application Data

[63] Continuation of Ser. No. 360,592, Dec. 21, 1994, abandoned.

[30] Foreign Application Priority Data

Dec. 24, 1993 [JP] Japan ..................................... 5-325650
Sep. 8, 1994 [JP] Japan ..................................... 6-214481

[51] Int. Cl.⁶ .................................................. H04N 7/18
[52] U.S. Cl. ................................ 348/68; 348/65; 348/66; 348/70
[58] Field of Search ................................. 348/65, 66, 67, 348/68, 69, 70, 71

[56] References Cited

U.S. PATENT DOCUMENTS

| | | | |
|---|---|---|---|
| 4,425,599 | 1/1984 | Rieder et al. | 362/32 |
| 4,951,134 | 8/1990 | Nakasima et al. | |
| 5,016,975 | 5/1991 | Sasaki et al. | 350/96 |
| 5,042,915 | 8/1991 | Akutsu et al. | 348/68 |
| 5,237,403 | 8/1993 | Sugimoto et al. | |
| 5,305,736 | 4/1994 | Ito | |
| 5,325,190 | 6/1994 | Nagasaki et al. | 348/270 |
| 5,339,159 | 8/1994 | Nakamura et al. | 348/71 |
| 5,475,420 | 12/1995 | Buchin | 348/65 |
| 5,488,509 | 1/1996 | Takahashi et al. | 359/385 |
| 5,627,583 | 5/1997 | Nakamura et al. | 348/72 |
| 5,631,695 | 5/1997 | Nakamura et al. | 348/65 |

FOREIGN PATENT DOCUMENTS 2181591  7/1990  Japan .

OTHER PUBLICATIONS

English Lnaguage Abstract of JP 2-181591.

*Primary Examiner*—Tommy P. Chin
*Assistant Examiner*—Anand Rao
*Attorney, Agent, or Firm*—Greenblum & Bernstein, P.L.C.

[57] ABSTRACT

A video endoscope system including a light guide for transmitting light emitted from a light source to illuminate an observation field of an endoscope, and a device for controlling the luminous flux of light supplied to the light guide from the light source. A solid-state imaging device forms an image of the observation field, and a processor processes an image signal output from the solid-state imaging device. In addition, a color tone correcting device divides the image to be processed by the processor into a plurality of regions and makes color tone correction with respect to each of the regions according to the control condition of the luminous flux control device.

22 Claims, 23 Drawing Sheets

VIDEO ENDOSCOPE SYSTEM WITH COLOR TONE CORRECTION

This application is a continuation of application Ser. No. 08/360,592, filed Dec. 21, 1994, now abandoned.

BACKGROUND OF THE INVENTION

The present disclosure relates to subject matter contained in Japanese Patent Application No. 5-325650 (filed on Dec. 24, 1993) and Japanese Patent Application No. 6-214481 (filed on Sep. 8, 1994), which are expressly incorporated herein by reference in their entireties.

1. Field of the Invention

The present invention relates to a video endoscope system designed so that the observation field of an endoscope is illuminated with illuminating light emitted from a light source and transmitted by a light guide, and an endoscope image signal in the observation field is taken out by a solid-state imaging device.

2. Description of the Prior Art

To obtain an observation image of good quality with a video endoscope system, it is necessary to optimize the brightness of illuminating light at all times.

Therefore, in a typical video endoscope system, the intensity of illuminating light is controlled by varying the voltage applied to the light source lamp, or controlling an aperture diaphragm which is provided in such a manner that it is movable into and out of an illuminating light path between the light source and the light guide, thereby enabling a favorable image brightness to be obtained at all times.

However, a change of the voltage applied to the light source lamp causes a change in the color temperature of the illuminating light. When the aperture diaphragm moves to change the position where it limits the cross-sectional area of the illuminating light path, spectral characteristics of illuminating light incident on the light guide from the light source change, resulting in a change of the color tone of the endoscope image.

Under these circumstances, the conventional practice is to correct the gain of each of the color image signals for three primary colors, i.e., red (R), green (G) and blue (B), according to the change of the light source voltage or the change in the aperture of the diaphragm, thereby making color tone correction of the endoscope image (see Japanese Patent Application Laid-Open (KOKAI) No. 2-181591).

However, more detailed analysis of the conventional technique has revealed that change in color tone of the endoscope image that occurs when the light source voltage is changed or when the aperture diaphragm is moved is not uniform throughout the screen image; there is a considerable difference in change of color tone between different portions of the screen image, e.g., between the central and peripheral portions of the screen image.

Such a phenomenon is attributable to the following reasons: The change in color temperature of the light source lamp that is caused when the light source voltage is changed differs between the central and peripheral portions of the screen image. The aperture diaphragm does not uniformly control the cross-sectional area of the illuminating light path but locally varies the cross-sectional area blocked by it. Therefore, the movement of the aperture diaphragm causes a change in the balance of light rays incident on the light guide at various angles. Thus, the above-described undesired phenomenon occurs on account of the light-transmitting characteristics of the light guide.

For the above reasons, color tone change occurring at every portion of the screen image is affected not only by the change of the light source voltage or the change in control condition of the aperture diaphragm but also by the characteristics of the light guide and the relationship between the light guide and the viewing optical system. That is, it also depends on the type of endoscope employed.

SUMMARY OF THE INVENTION

An object of the present invention is to provide a video endoscope system capable of obtaining favorable color reproducibility throughout the endoscope image independent of the change of the light source voltage or the change in control condition of the aperture diaphragm, which limits the cross-sectional area of the illuminating light path, and the type of endoscope employed.

Other objects and advantages of the present invention will become apparent from the following detailed description of illustrated embodiments of the invention.

According to the present invention, there is provided a video endoscope system including a light guide for transmitting illuminating light emitted from a light source to illuminate the observation field of an endoscope, and a device for controlling the luminous flux of illuminating light supplied to the light guide from the light source. A solid-state imaging device takes an image in the observation field, and a processor processes an image signal output from the solid-state imaging device. In addition, a color tone correcting device divides the image to be processed by the processor into a plurality of regions and makes color tone correction with respect to each of the regions according to the control condition of the luminous flux control device.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
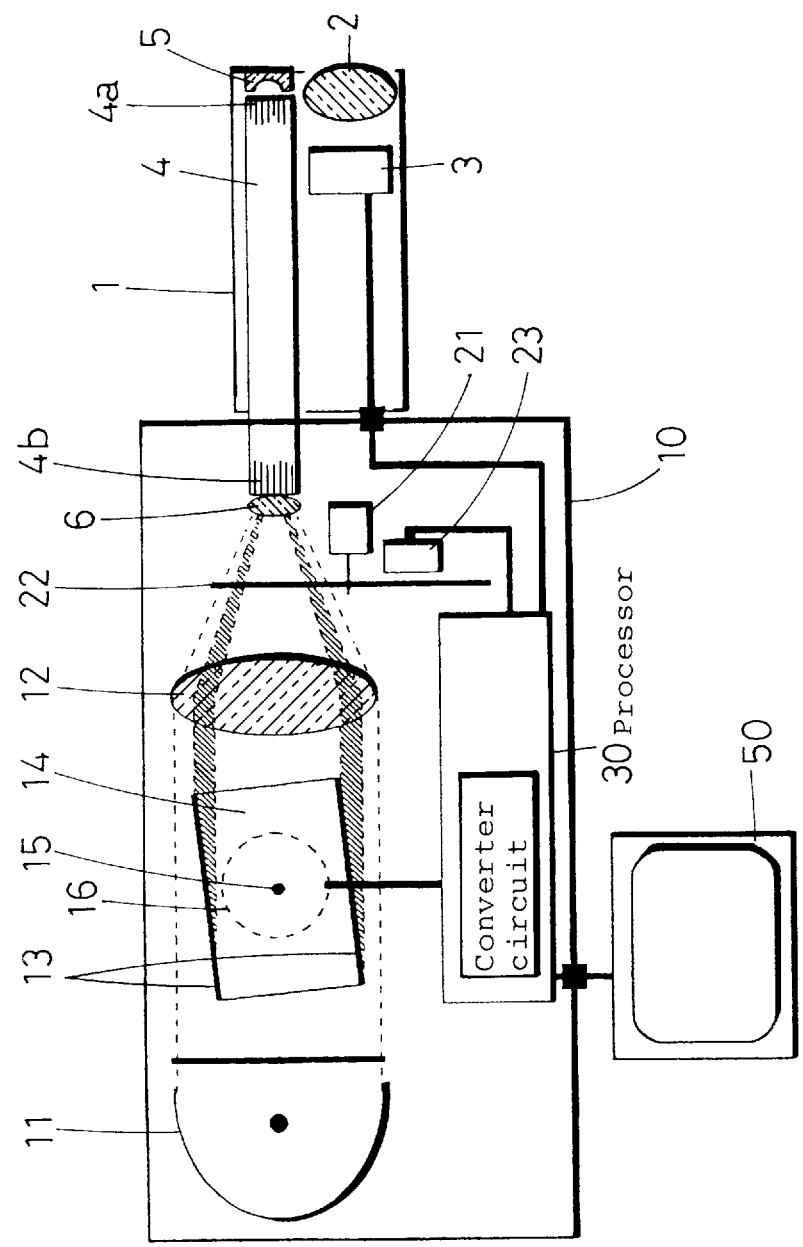
FIG. 1 schematically shows the arrangement of a video endoscope system according to a first embodiment of the present invention.

FIG. 1 shows a video endoscope system according to a first embodiment of the present invention. An endoscope 1 has an objective lens 2 disposed in the distal end of an insert part thereof. A solid-state imaging device 3, e.g., a CCD (Charge-Coupled Device), is disposed such that a light-receiving surface thereof lies at a position where an image of an object is formed by the objective lens 2.

An illuminating light guide fiber bundle 4 transmits light for illuminating the visual field of the objective lens 2. Thus, a part which is under observation is illuminated with light emerging from an exit end portion 4a of the light guide fiber bundle 4 and passing through a concave lens 5.

A light source apparatus 10 with a video processor supplies illuminating light to the light guide fiber bundle 4. An entrance end portion 4b of the light guide fiber bundle 4 is detachably inserted into the light source apparatus 10.

Illuminating light is emitted in the form of a bundle of parallel rays from a light source lamp 11 disposed in the light source apparatus 10. The illuminating light is converged by a converging lens 12 so as to enter the entrance end portion 4b of the light guide fiber bundle 4. An entrance lens 6 is disposed at the entrance end portion 4b of the light guide fiber bundle 4.

In an illuminating light path between the light source lamp 11 and the converging lens 12, a pair of opaque, parallel flat plates 13 are disposed in parallel to the optical axis of the illuminating light path so that a part or the whole of the bundle of illuminating light rays reaching the converging lens 12 can be intercepted. Thus, the parallel flat plates 13 constitute an aperture diaphragm.

Figure 2:
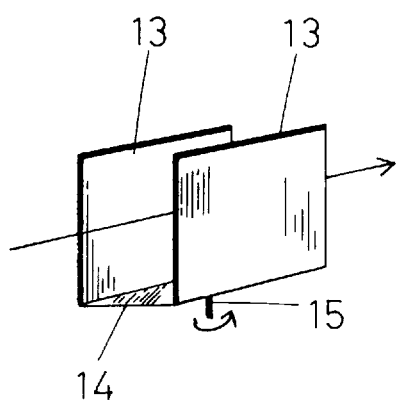
FIG. 2 is a perspective view of an aperture diaphragm.

As shown, for example, in FIG. 2, the pair of parallel flat plates 13 are rectangular plates of the same size. The parallel flat plates 13 are connected together by a connecting plate 14 to form an integral structure having a U-shaped cross-sectional configuration.

A rotating shaft 15 is rigidly connected to the center of the bottom of the connecting plate 14 so as to extend in a direction perpendicular to the optical axis of the illuminating light path and parallel to the parallel flat plates 13. By rotating the rotating shaft 15 with a step motor 16, for example, the parallel flat plates 13 can be rotated so as to change the direction thereof and stopped at a desired position.

The rotation of the parallel flat plates 13 causes a change in the cross-sectional area of the bundle of illuminating light rays that is blocked by these plates 13. Thus, it is possible to change the luminous flux (brightness) of illuminating light entering the light guide fiber bundle 4.

As shown in FIG. 1, a filter disk 22 is disposed in the illuminating light path between the entrance end portion 4b of the light guide fiber bundle 4 and the converging lens 12. The filter disk 22 is driven to rotate in one direction at a constant speed by a motor 21.

The filter disk 22 has three color filters for red (R), green (G) and blue (B), which are circumferentially spaced so that these color filters sequentially lie in the illuminating light path. Consequently, the field of observation with the objective lens 2 is illuminated sequentially with light rays of the three colors.

A filter detector 23 is disposed to face the filter disk 22 so as to detect the position of each color filter of the filter disk 22. The result of the detection is input to a processor 30.

The processor 30 controls input/output signals of the solid-state imaging device 3 and processes an endoscope image signal sent from the solid-state imaging device 3. That is, the processor 30 executes field-sequential image pickup processing in which images taken with illuminating light rays of the three colors in time-sharing manner are combined into one composite image. On the basis of an image signal that is output as a result of the processing, a full-color endoscope image of an object in the observation field is displayed on a monitor 50.

The processor 30 also outputs a control signal to the motor 16 for driving the aperture diaphragm 13, thereby controlling the luminous flux of illuminating light entering the light guide fiber bundle 4.

Figure 3:
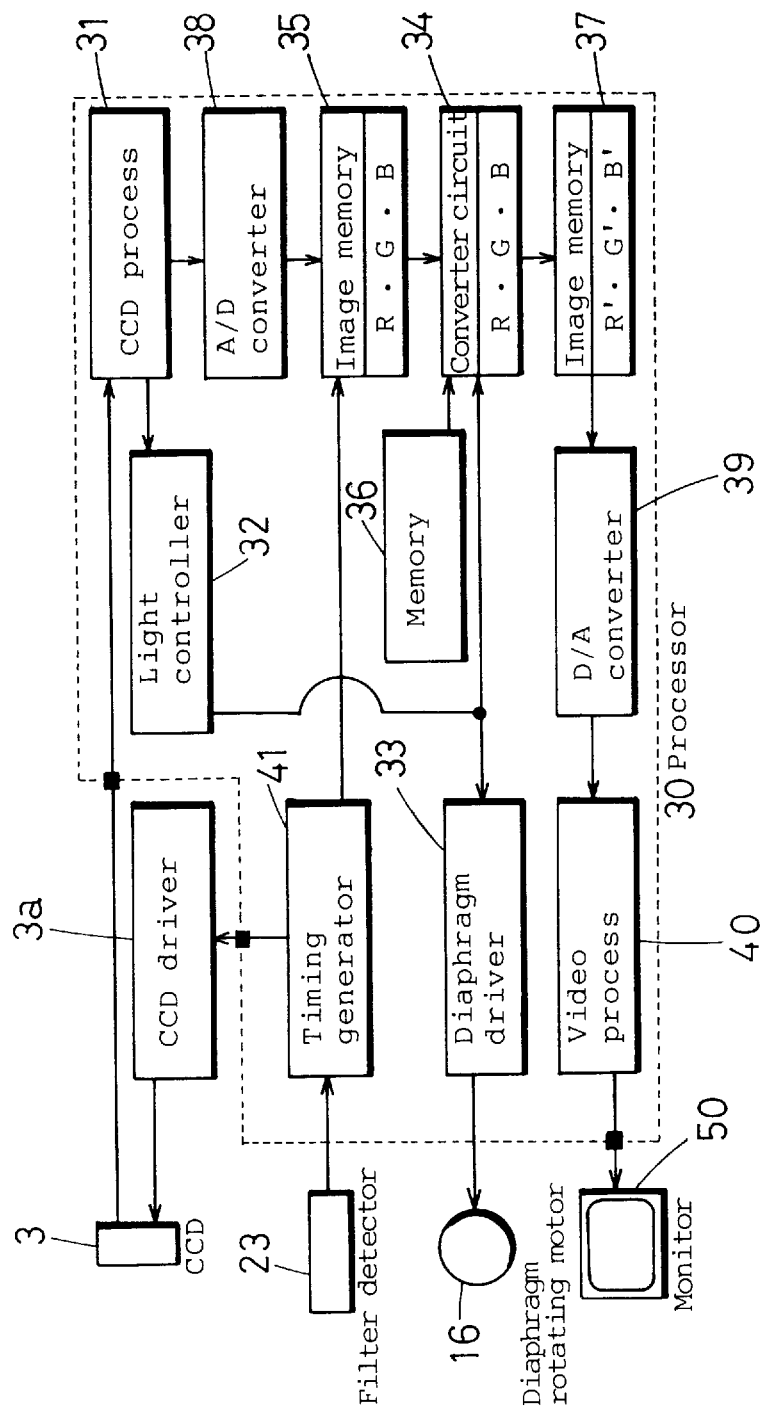
FIG. 3 schematically shows the arrangement of a processor and peripheral units attached thereto in the first embodiment.

FIG. 3 shows the arrangement of the processor 30 and peripheral units attached thereto. An endoscope image signal sent from the solid-state imaging device (CCD) 3 is input to a CCD process circuit 31 where it is subjected to predetermined processing. According to an output signal from the CCD process circuit 31, an angle of rotation of the aperture diaphragm 13 (i.e., a ray bundle intercepting condition of the aperture diaphragm 13 with respect to the illuminating light path) is determined in a light controller circuit 32.

The information on the rotational angle of the aperture diaphragm 13 is sent to a diaphragm driver circuit 33 to drive the diaphragm rotating motor 16. The information on the diaphragm angle, which has been determined in the light controller circuit 32, is also sent to a converter circuit 34.

The converter circuit 34 is associated with an image memory 35 in which endoscope image information is stored for each of the three colors, i.e., red (R), green (G) and blue (B). The converter circuit 34 converts the stored information according to conversion data stored in a memory 36, and stores the converted information in a second image memory 37.

The image signal from the CCD process circuit 31 is supplied through an A/D converter circuit 38 to the image memory 35 where it is stored in each of R, G and B memories.

The converter circuit 34 calls color conversion information from the memory 36 according to the diaphragm angle and executes data conversion on the basis of the conversion information for each of R, G and B images. Thus, color tone correction of the endoscope image is made.

The converted information is sent from the image memory 37 to a video process circuit 40 through a D/A converter circuit 39 and output to the monitor 50 as an NTSC signal, for example.

A timing generator 41 generates a synchronizing signal on the basis of the detection signal from the filter detector 23 and outputs it to a CCD driver circuit 3a and the image memory 35.

Figure 4:
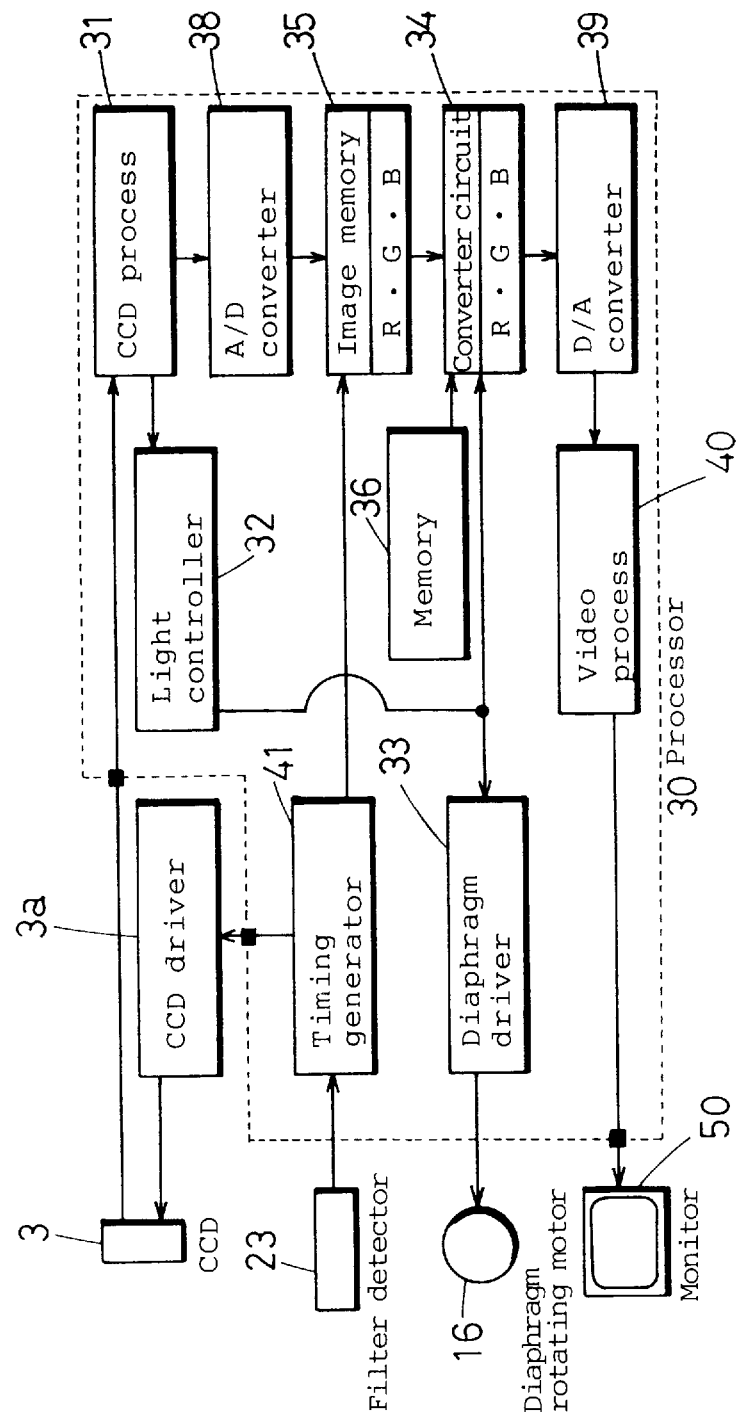
FIG. 4 schematically shows another example of the arrangement of a processor and peripheral units attached thereto in the first embodiment.

It should be noted that the processor 30 may be arranged such that the output signal from the converter circuit 34 is transmitted directly to the D/A converter circuit 39, as shown in FIG. 4. Since the second image memory 37 is not needed in the alternative arrangement, the parts cost can be correspondingly reduced.

Figure 5:
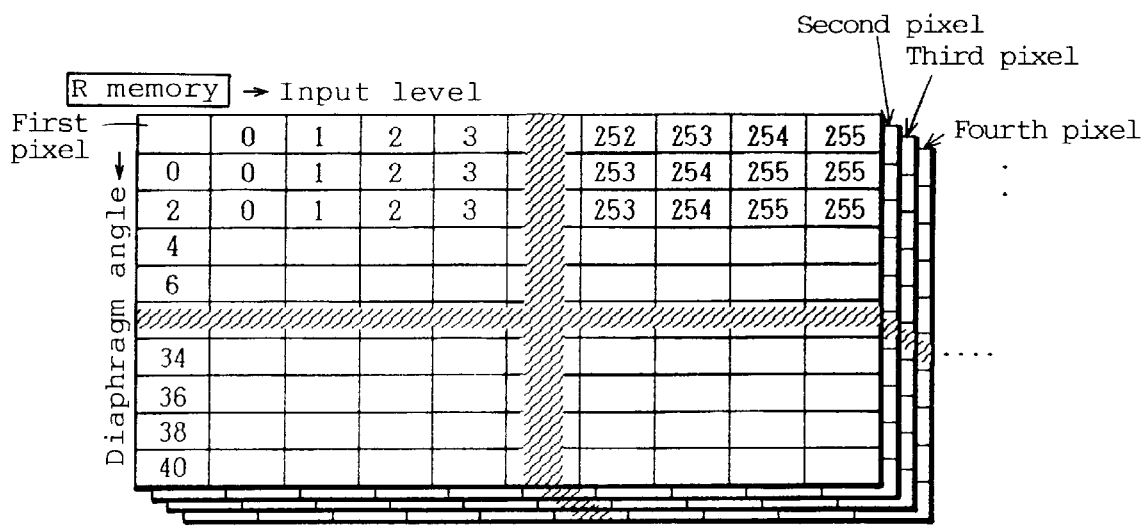
FIG. 5 schematically shows look-up tables in the first embodiment.

The color conversion information is stored in the memory 36 in the form of LUT (Look-Up Table) as shown in FIG. 5. In this example, there are provided a number of tables which corresponds to the total number of pixels of an endoscope image on the image memory 35. The tables are arranged such that the first table stores color conversion information for the first pixel of the endoscope image, the second table for the second pixel, and so forth.

Each table is divided in both vertical and horizontal directions. In the vertical direction, the corresponding diaphragm angles are shown; in the horizontal direction, the memory values obtained are shown. For example, when the diaphragm angle is 2 degrees, and the input level at the first pixel is 254, the value of 255 is output as a result of conversion according to the table.

The memory 36 is provided with a total of 3 sets of tables such as those described above for R, G and B, so that color tone correction is made with respect to each pixel on the image memory 35 by the converter circuit 34.

Figure 6:
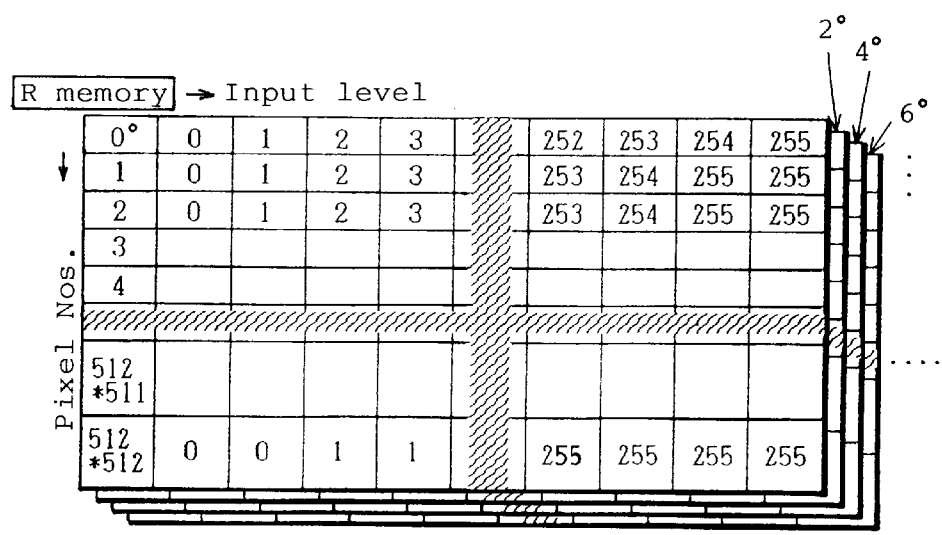
FIG. 6 schematically shows look-up tables in the first embodiment.

It is also possible to use LUTs in which, as shown in FIG. 6, the first table stores color conversion information for the diaphragm angle of zero degree, the second table for the angle of two degrees, and so forth, and in which the pixels are listed in the vertical direction in ascending order, i.e., the first pixel, the second pixel, and so forth (actual LUT is held on the memory 36 in the form of array).

Figure 7:
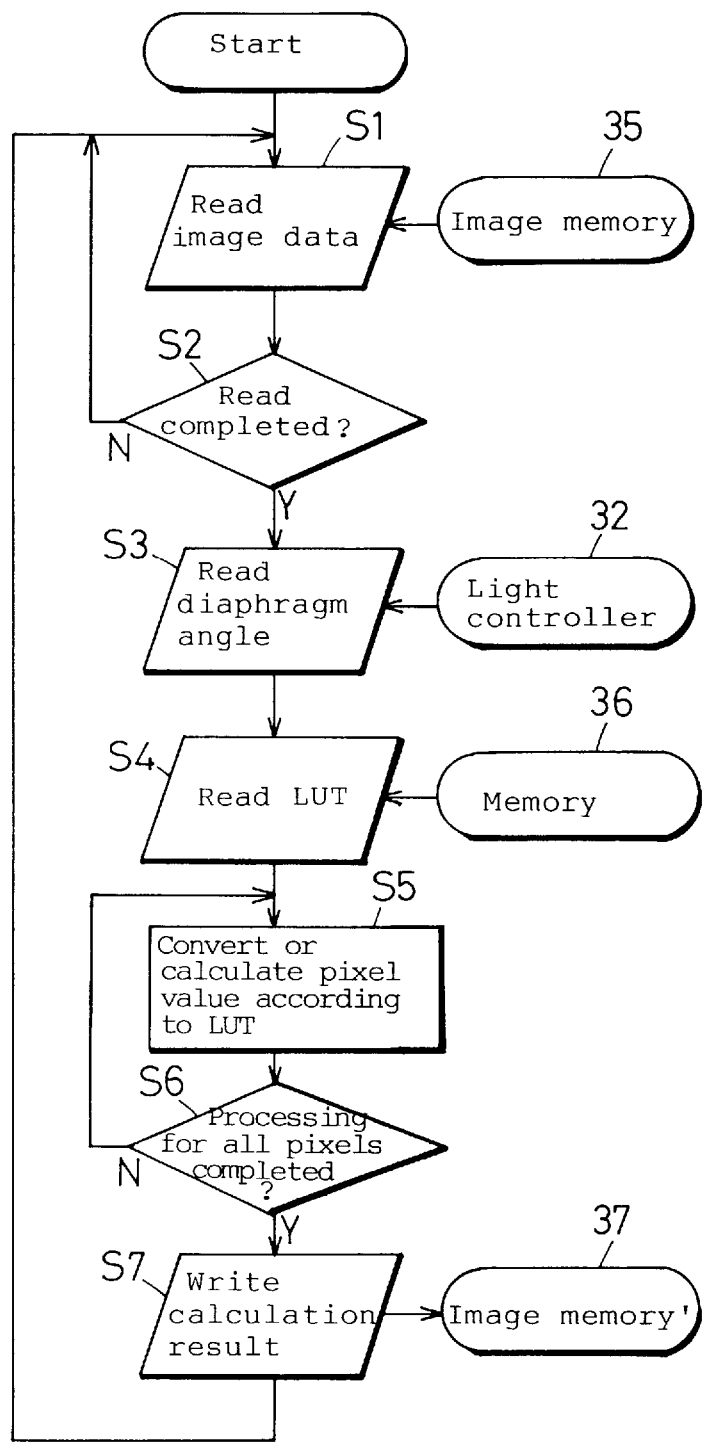
FIG. 7 is a flowchart showing color tone correction processing in the first embodiment.

FIG. 7 is a flowchart showing color tone correction processing in this embodiment, in which reference symbol S denotes processing steps. First, all of R, G and B image data for one frame of image is read from the image memory 35 (S1 and S2). Then, the angle of the diaphragm 13 is read from the light controller circuit 32 (S3).

Subsequently, conversion data corresponding to the diaphragm angle is read from the LUT in the memory 36 (S4), and conversion or calculation of the pixel value is executed according to the data read from the LUT (S5). Upon completion of the processing for all the pixels (S6), the result of the processing is output to the second image memory 37 (S7). Then, the process shifts to processing for the next image.

Figure 8:
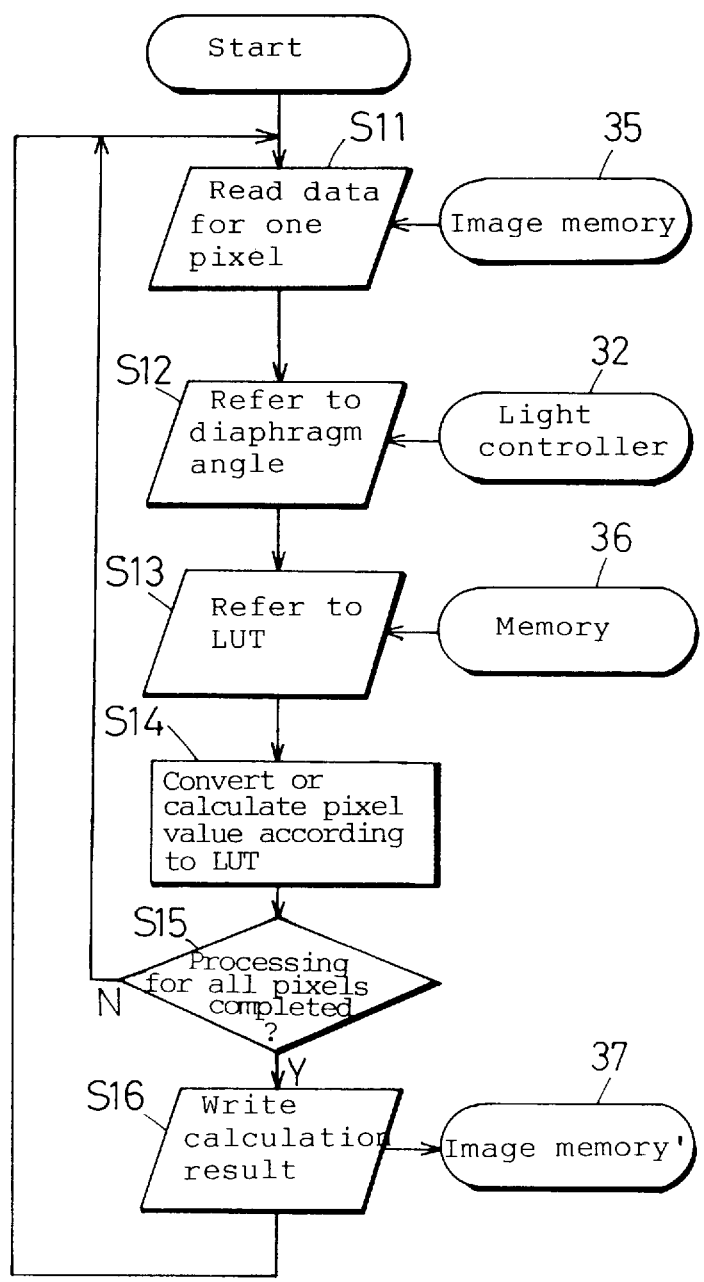
FIG. 8 is a flowchart showing color tone correction processing in the first embodiment.

FIG. 8 is a flowchart showing an example of processing substitutable for the processing shown in FIG. 7. In this example, after image data for one pixel read from the image memory 35 has been converted according to data in the LUT, image data for the subsequent pixel is processed (S11 to S14). Upon completion of the processing for all the pixels (S15), the result of the processing is output to the second image memory 37 (S16). Then, processing for the next image is initiated.

Figure 9:
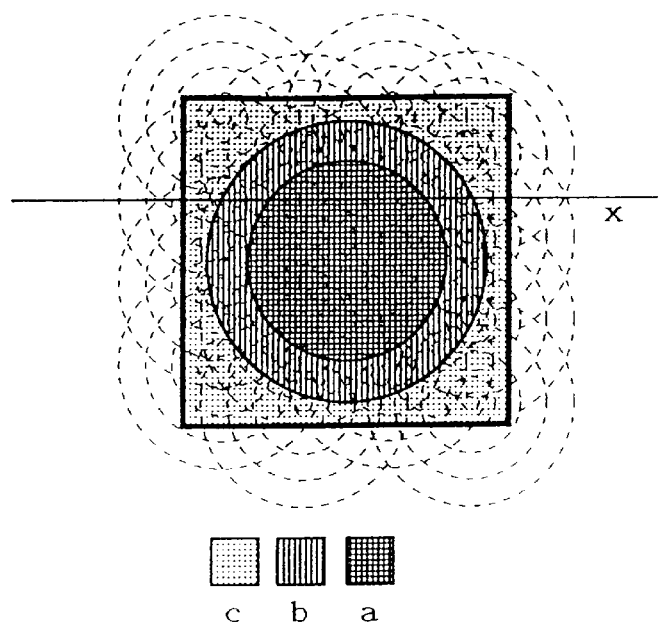
FIG. 9 is a schematic view for explanation of a brightness distribution on an endoscope image.

Let us consider one line on an endoscope image taken with illuminating light passing through a certain color filter, and assume the line to be a line x with respect to a square endoscope image as shown in FIG. 9.

Figure 10:
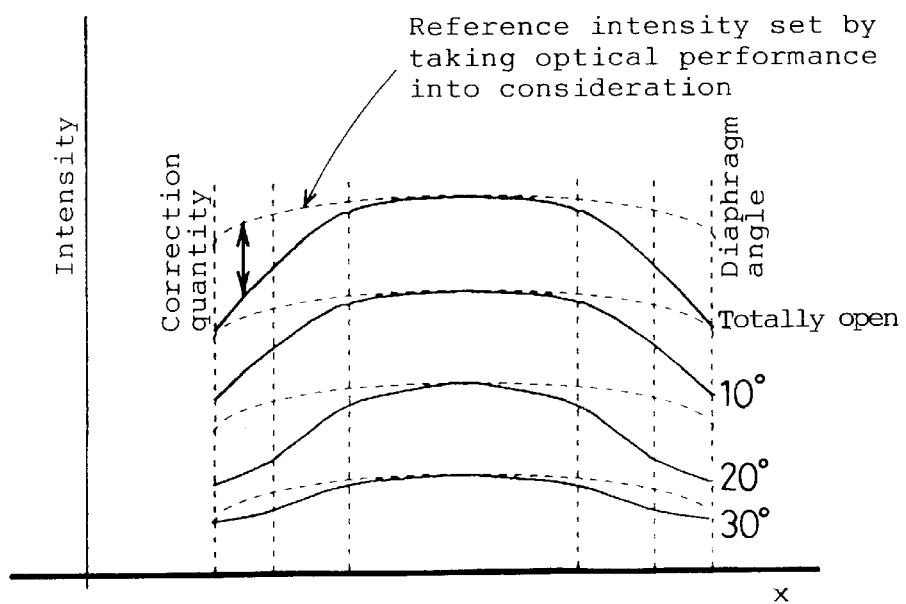
FIG. 10 is a graph showing correction characteristic curves in the first embodiment.

In this case, the intensity (or CCD output signal or quantization level) at each pixel is such as that shown by the solid lines in FIG. 10. At the left- or right-hand end (where x is relatively small or large), the intensity is lower than that at the central portion. The intensity ratio between the central and peripheral portions also changes according to the angle of the diaphragm 13.

Considering characteristics of the illuminating and imaging optical systems, e.g., lowering in the marginal illumination, the error, that is, the difference between the ideal intensity curve (broken line) and the actual intensity curve (solid line), should be taken into account and used as a correction quantity. By scanning the endoscope image (shown in FIG. 9) with the line x from the top to the bottom, correction data for each pixel can be obtained, and thus LUTs can be prepared.

Figure 15:
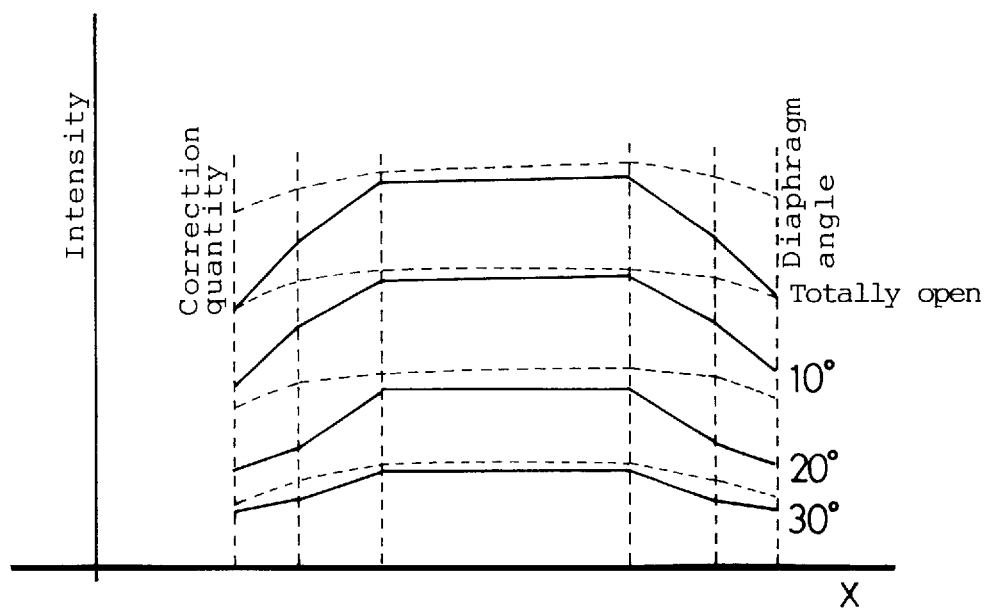
FIG. 15 is a graph showing correction characteristic curves in the first embodiment.

It should be noted that LUTs are not necessarily limited to those shown in FIGS. 5 and 6, and that conversion data may be defined as coefficients of the curves (curved surfaces on the endoscope image) as shown in FIG. 10. In this case, calculation is performed for each pixel in the converter circuit 34 shown in FIG. 3. The curves shown in FIG. 10 may be replaced by approximate curves which are set so as to vary rectilinearly, as shown in FIG. 15.

Next, a second embodiment of the present invention will be explained.

It may be considered that color tone variation of illuminating light as shown in FIG. 9 occurs substantially equally in each of regions divided by concentric circles, i.e., regions denoted by a, b and c in the figure.

Figure 11:
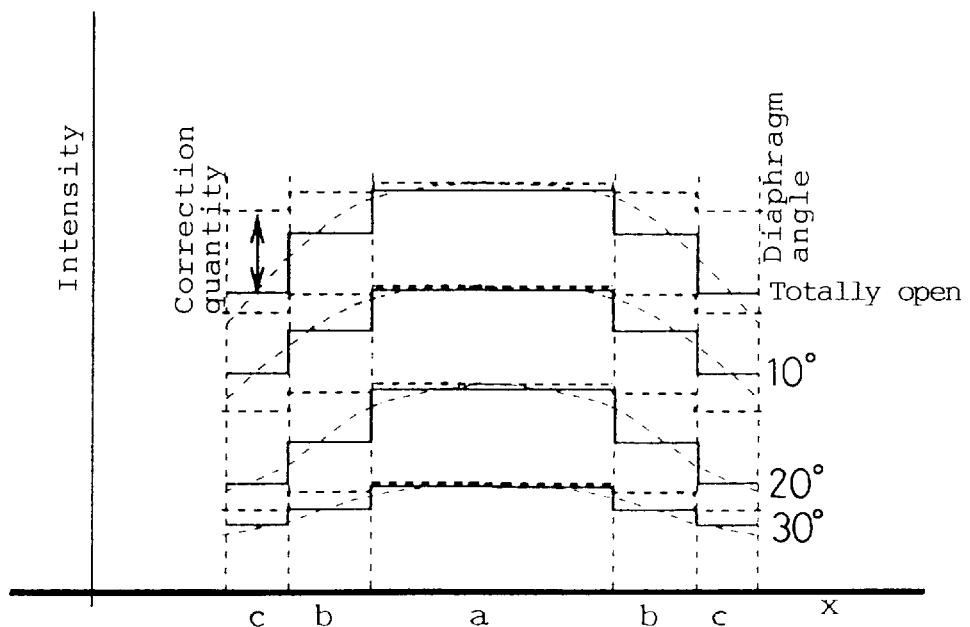
FIG. 11 is a graph showing correction characteristic curves in a second embodiment.

Therefore, the intensity curve may be approximated by a step-shaped solid line as shown in FIG. 11. If the ideal approximate curve is also set in the form of a step-shaped curved line, the correction quantities in each region can be equalized. Division of the endoscope image into regions may be made by circles or polygons. The number of divided regions may be any number not smaller than 2. If the endoscope image is divided into regions in this way, color tone correction can be made without referring to LUT for each pixel. Accordingly, the processing time can be shortened by a considerable extent.

Figure 12:
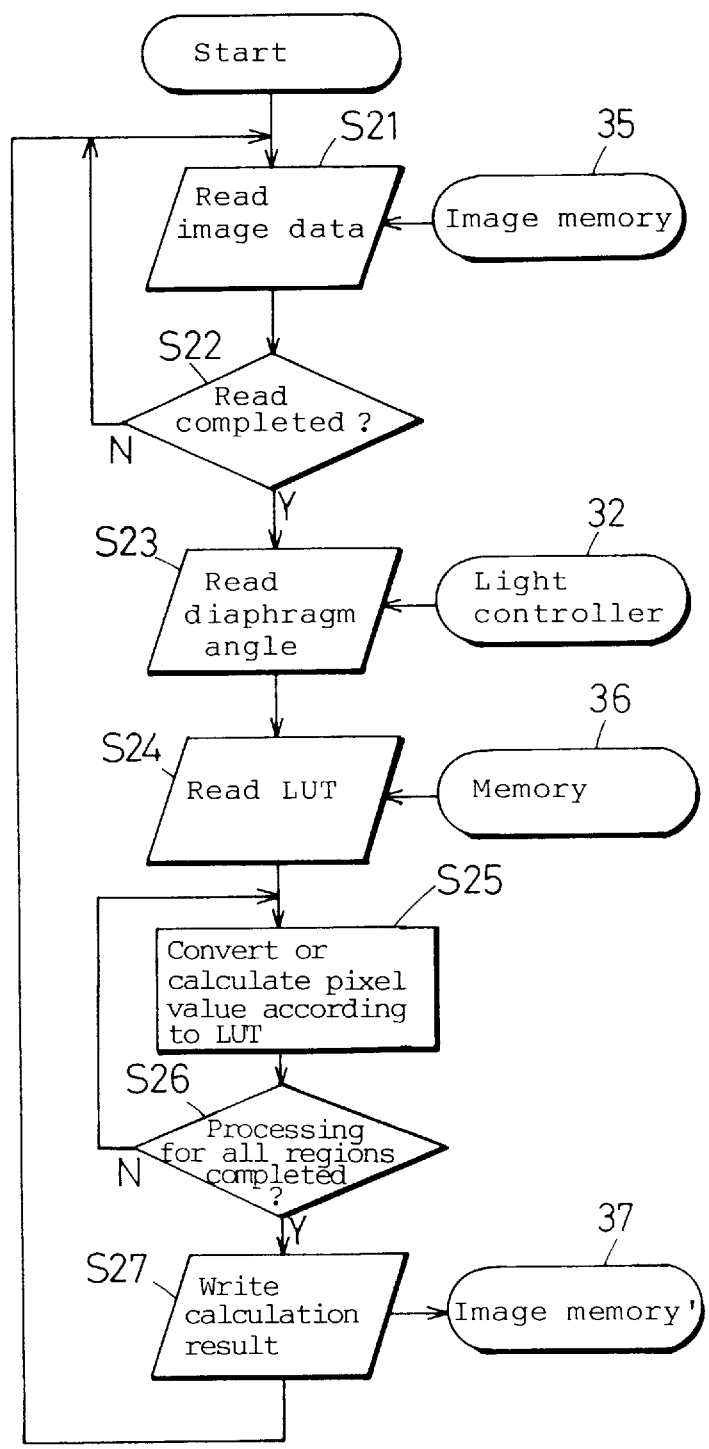
FIG. 12 is a flowchart showing color tone correction processing in the second embodiment.
Figure 13:
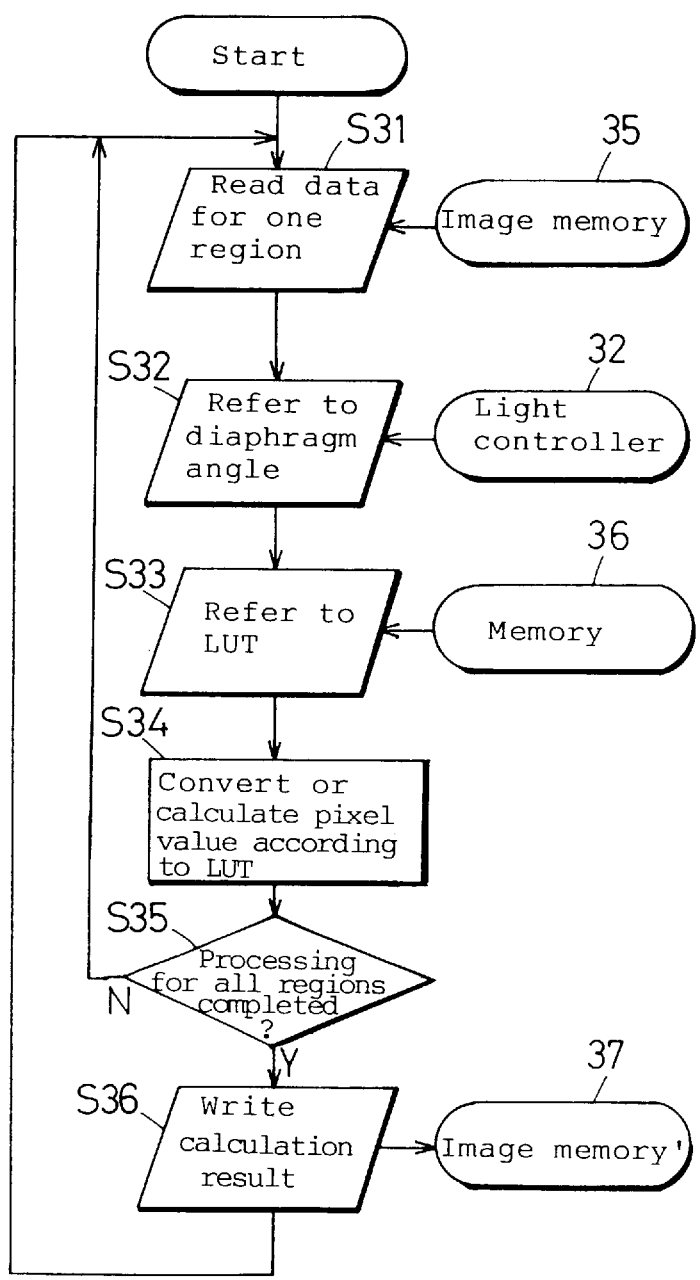
FIG. 13 is a flowchart showing color tone correction processing in the second embodiment.
Figure 14:
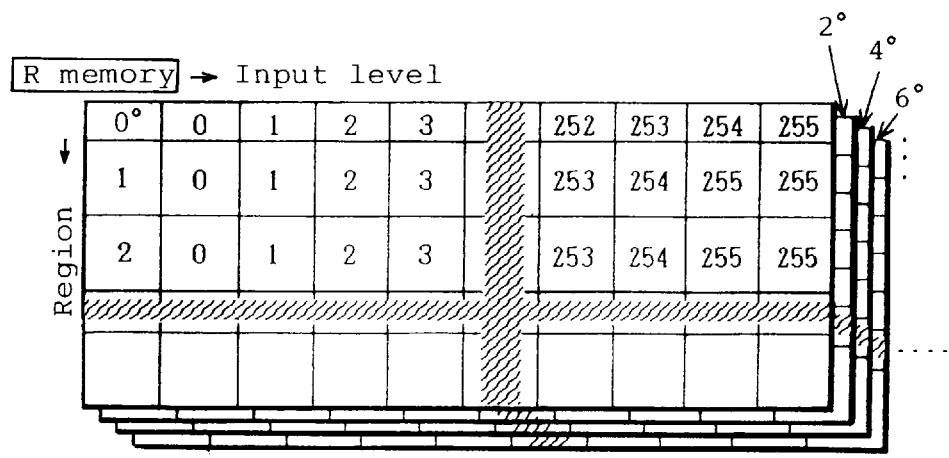
FIG. 14 schematically shows look-up tables in the second embodiment.

FIGS. 12 and 13 are flowcharts showing color tone correction processing in the second embodiment. FIG. 14 shows LUTs in the second embodiment. The flowcharts and LUTs in the second embodiment are the same as those in the first embodiment except that, in the second embodiment, processing is executed in units of regions, whereas, in the first embodiment, it is executed in units of pixels. Therefore, detailed description thereof is omitted.

Next, a third embodiment of the present invention will be explained.

In the above-described embodiments, color tone variation due to the angle of the diaphragm 13 and the characteristics of the light guide fiber bundle 4 is corrected by using the memory 36 having one set of LUTs.

However, the angle of the diaphragm 13 is an intrinsic factor of the light source apparatus 10, whereas the light guide fiber bundle 4 is an intrinsic factor of the endoscope 1. Moreover, in many cases a plurality of different types of endoscope 1 are interchangeably connected to the same light source apparatus 10.

Therefore, in this embodiment, a first LUT for correction of color tone variation depending on the angle of the diaphragm 13 is provided in the light source apparatus 10, while a second LUT for correction of color tone variation depending on the light guide fiber bundle 4 is provided in the endoscope 1.

Figure 16:
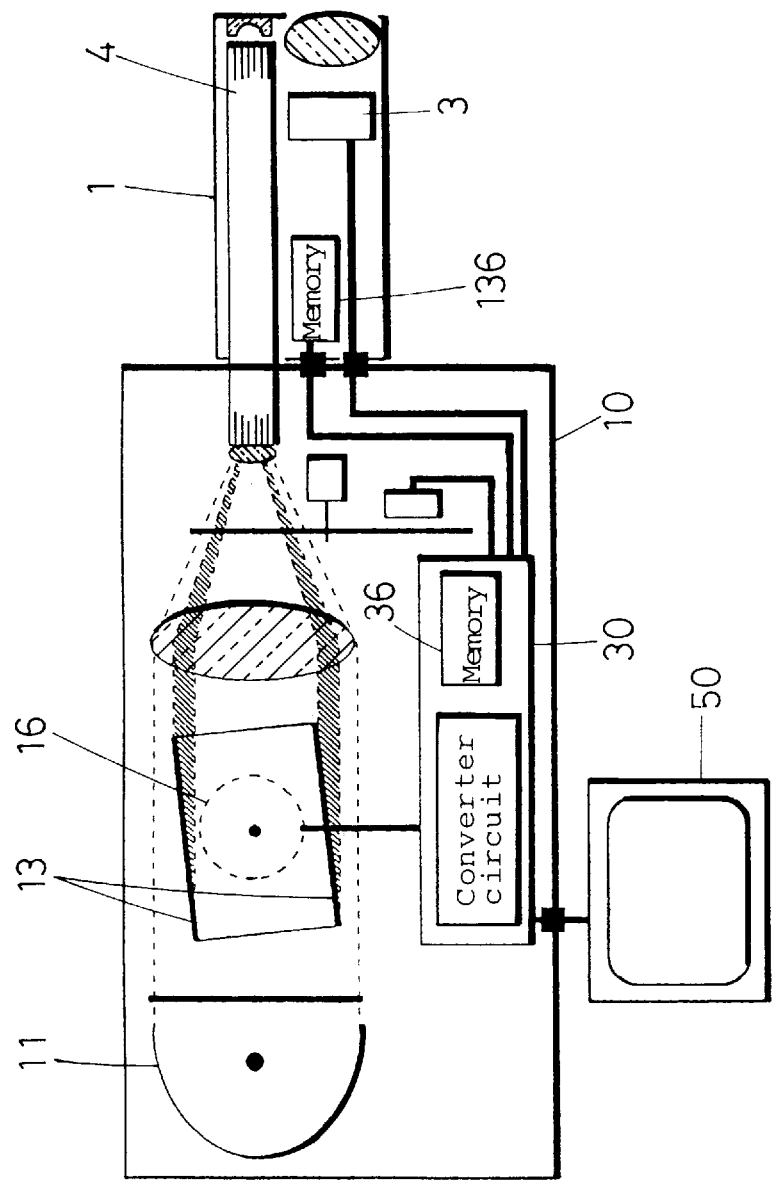
FIG. 16 schematically shows the arrangement of a video endoscope system according to a third embodiment of the present invention.

FIG. 16 shows a video endoscope system according to this embodiment, in which a memory 136 stored with the second LUT is provided in the endoscope 1 such that the memory 136 can be connected to the processor 30.

Figure 17:
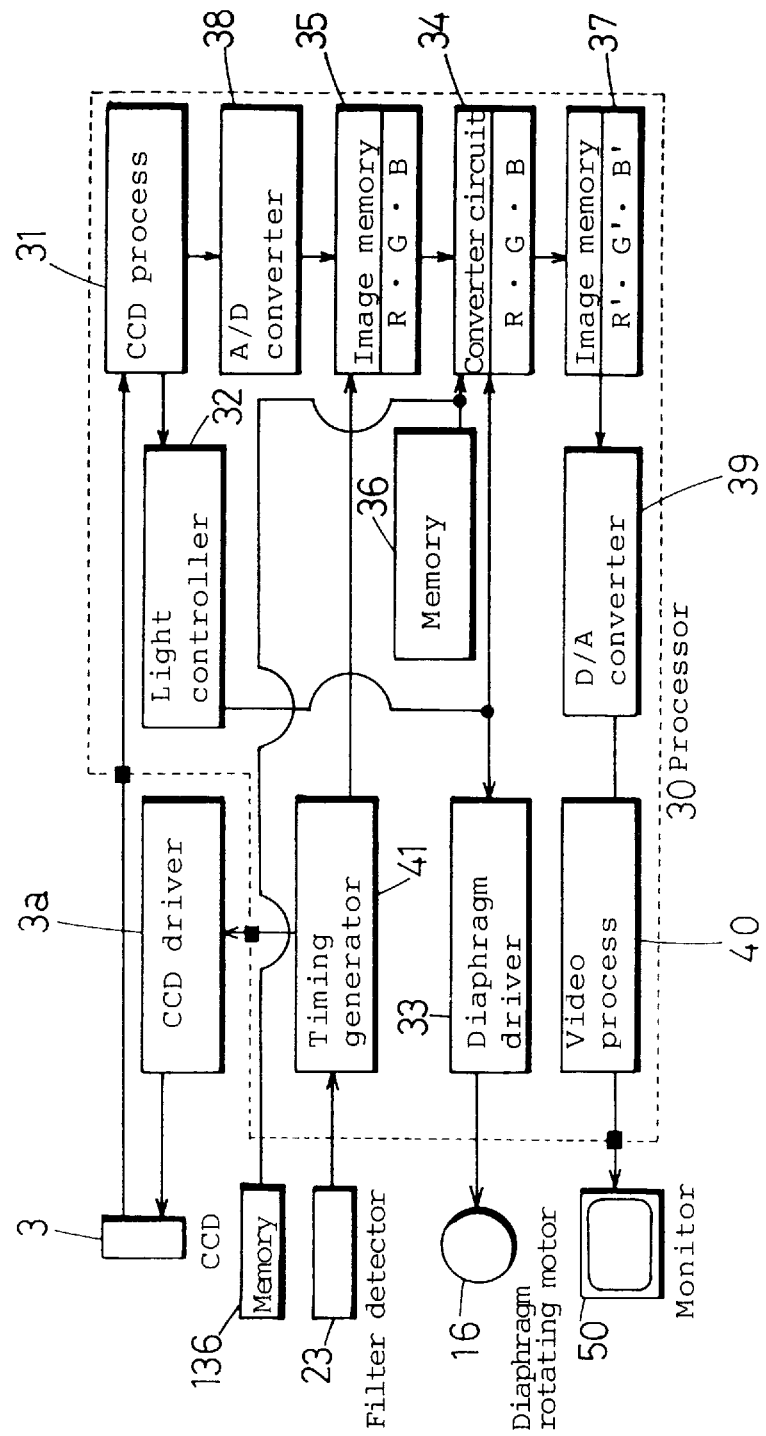
FIG. 17 schematically shows the arrangement of a processor and peripheral units attached thereto in the third embodiment.
Figure 18:
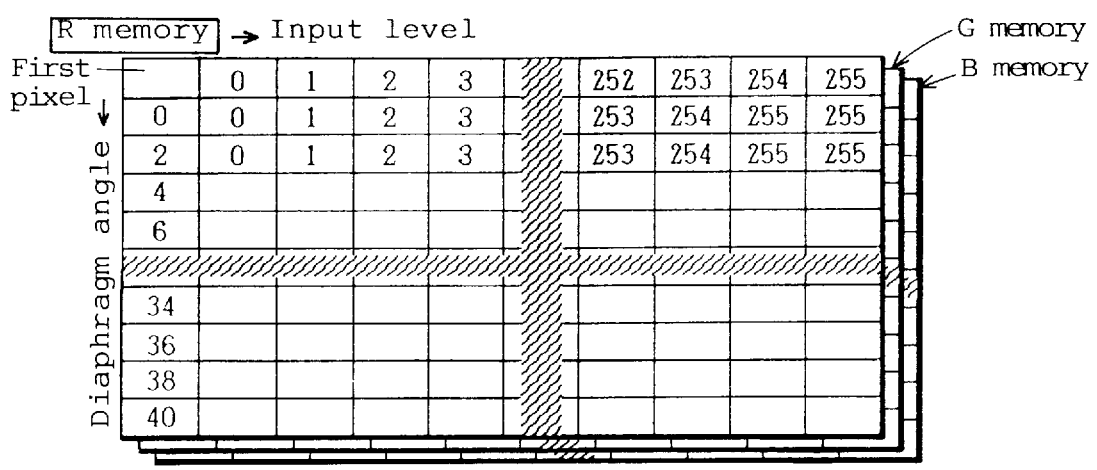
FIG. 18 schematically shows look-up tables in the third embodiment.

FIG. 17 shows the arrangement of the processor 30 and peripheral units attached thereto in this embodiment. In this embodiment, the second memory 136 is added to the arrangement of the first embodiment. The second memory 136 is connected to the converter circuit 34. FIG. 18 shows an example of the LUT provided in the endoscope 1. The LUT provided in the light source apparatus 10 may be the same as that shown in FIG. 6.

Figure 19:
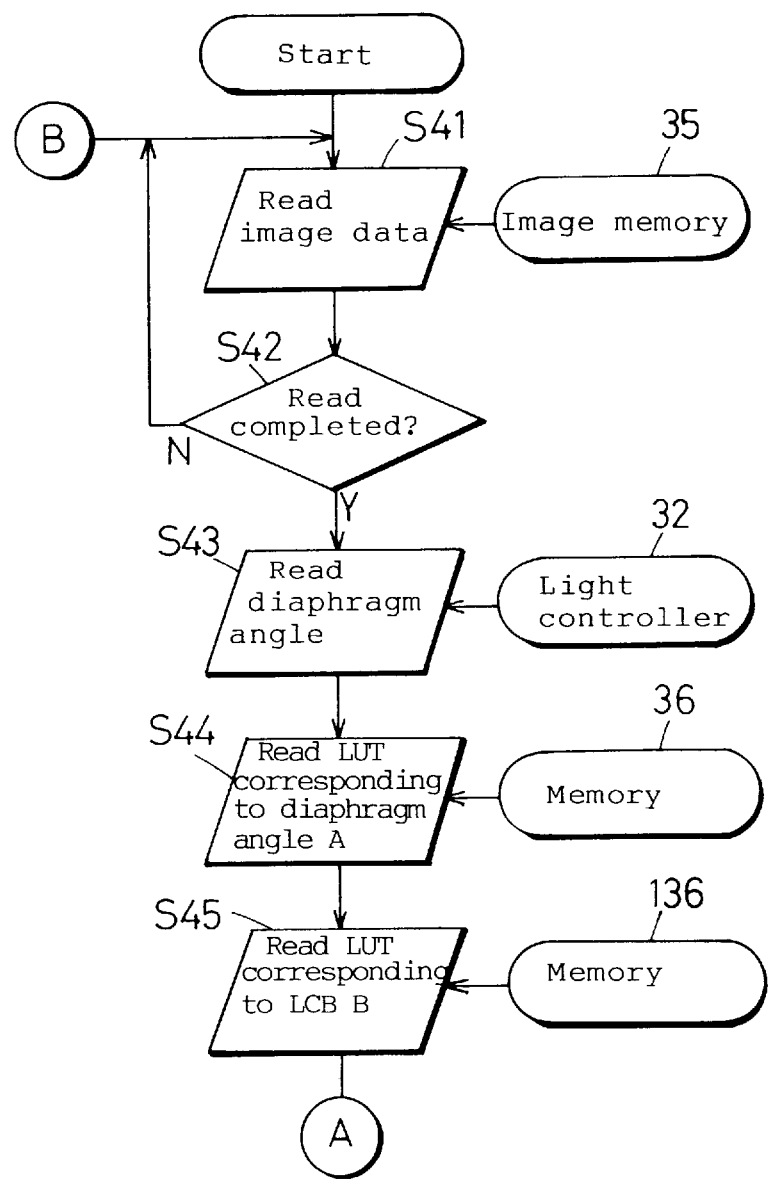
FIG. 19 is a flowchart showing color tone correction processing in the third embodiment.
Figure 20:
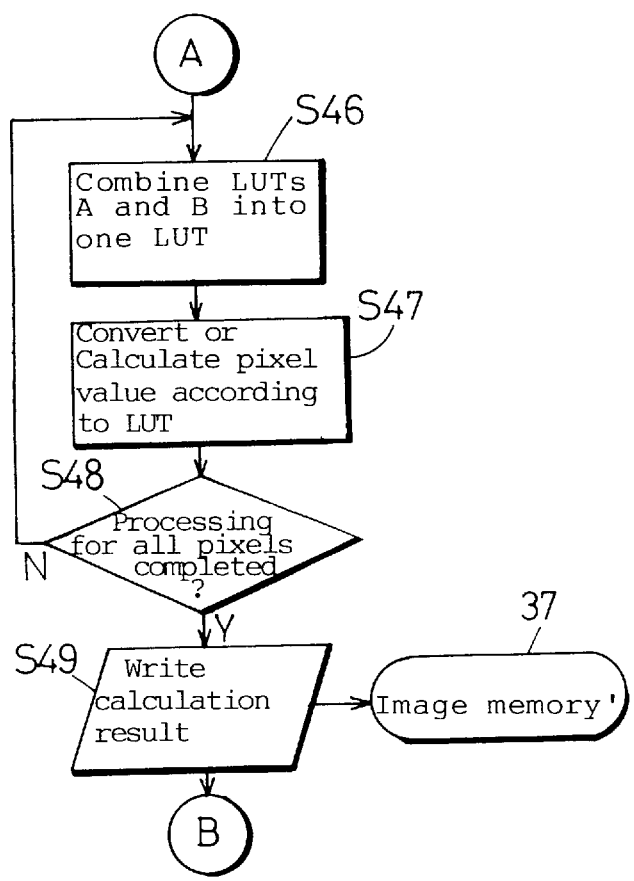
FIG. 20 is a flowchart showing color tone correction processing in the third embodiment.

FIGS. 19 and 20 are flowcharts showing color tone correction processing in which data read from the two LUTs, which are provided in the light source apparatus 10 and the endoscope 1, are combined together in the converter circuit 34 to handle the two LUTS as a single LUT. Data is sequentially read from the two LUTs at S44 and S45, and combined together to form a single LUT at S46. The other steps are the same as those in the processing of the first embodiment shown in FIG. 7.

Figure 21:
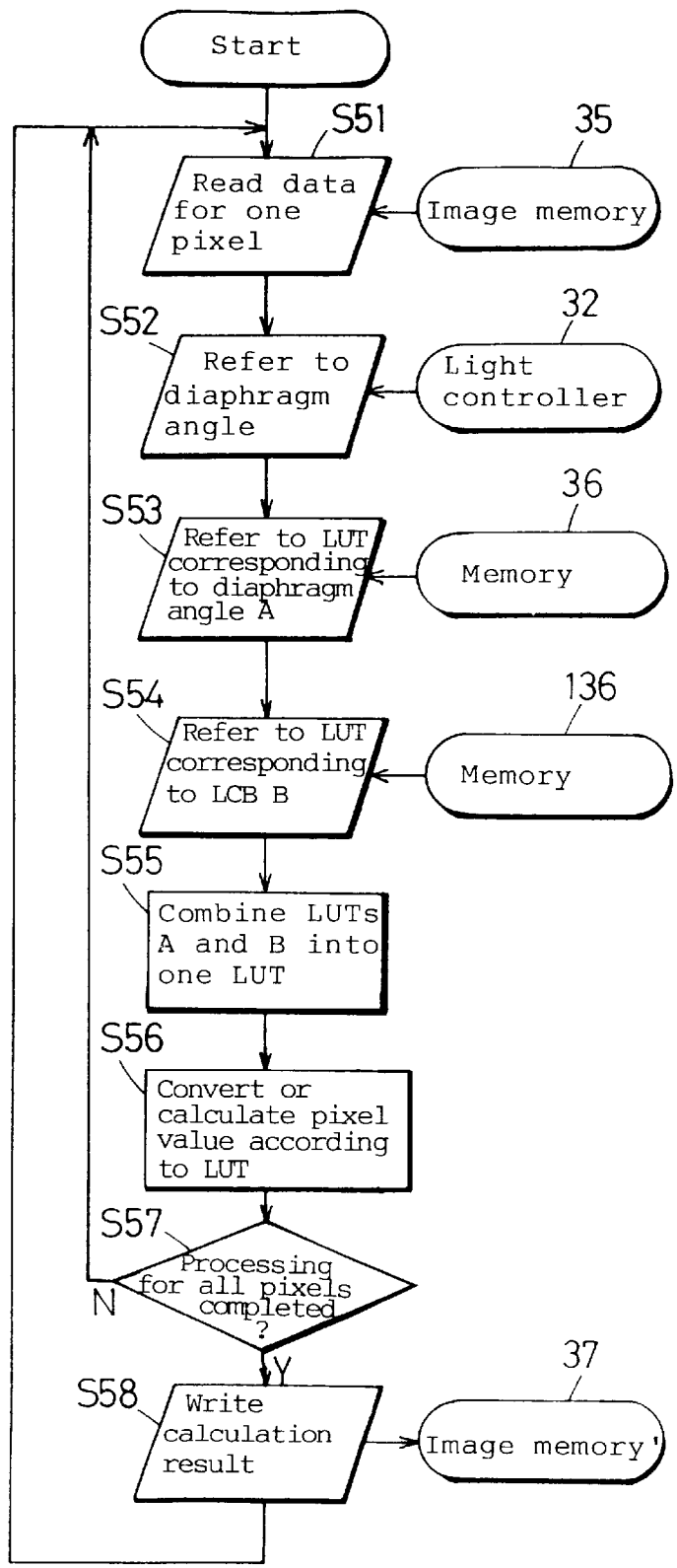
FIG. 21 is a flowchart showing color tone correction processing in the third embodiment.

FIG. 21 shows processing in a case where input and conversion of data are successively executed for each pixel. It should be noted that "LCB" in FIGS. 19 and 21 means the light guide fiber bundle 4.

Figure 22:
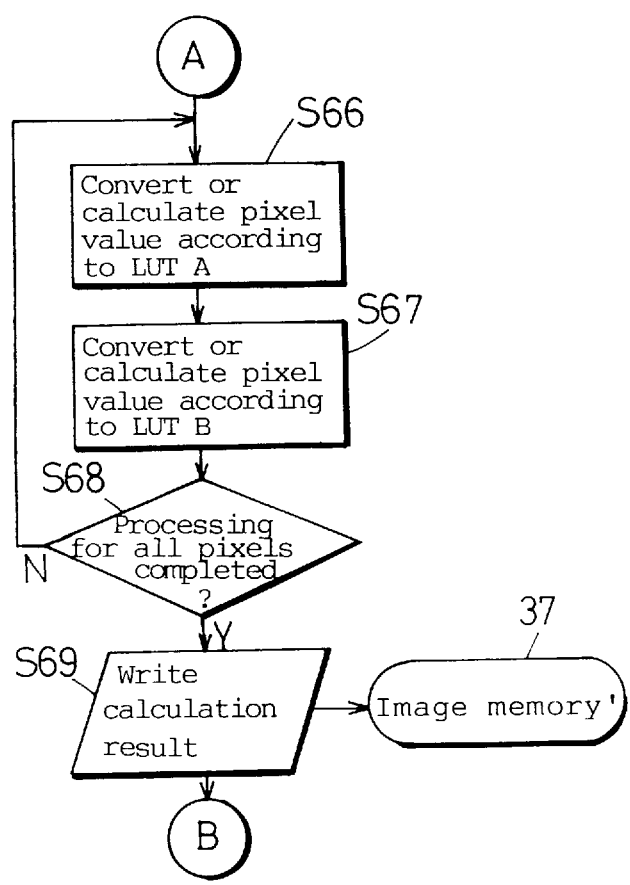
FIG. 22 is a flowchart showing color tone correction processing in the third embodiment.
Figure 23:
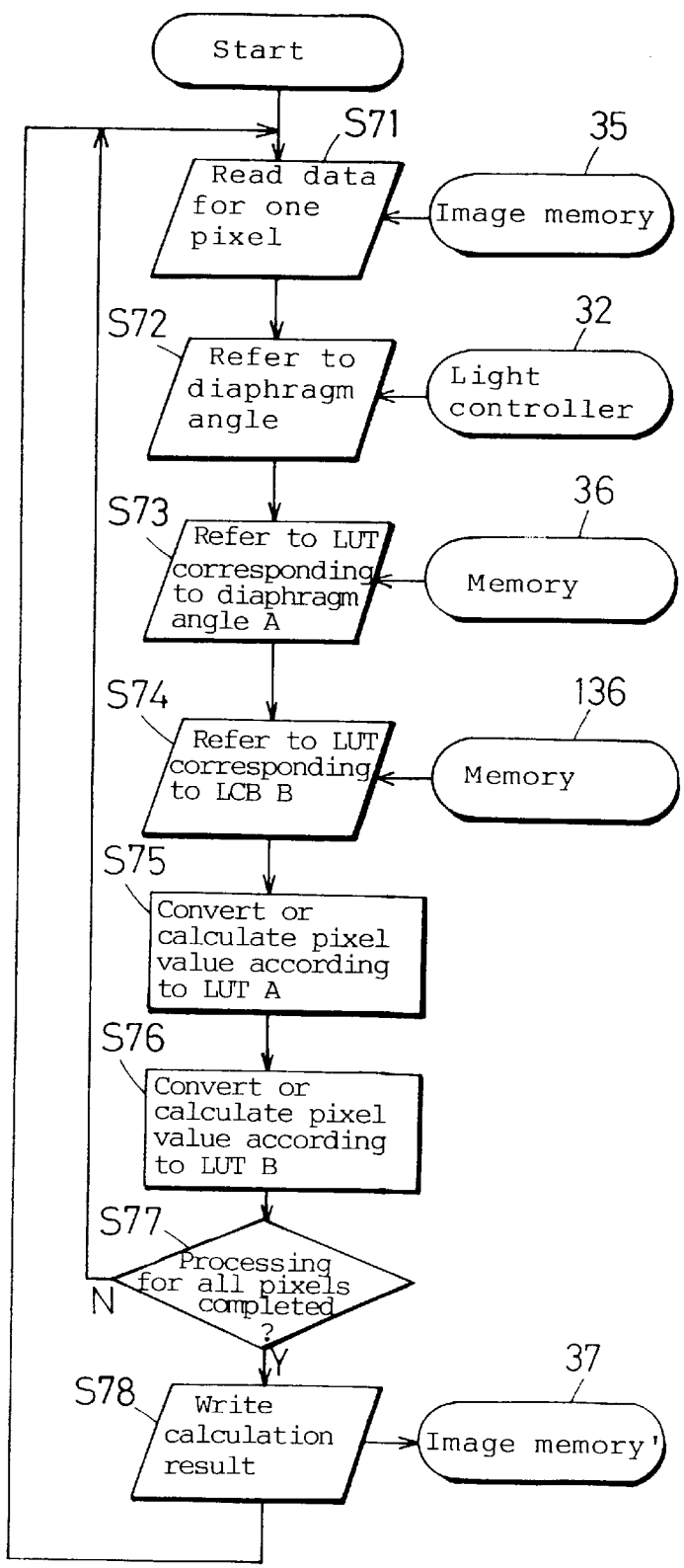
FIG. 23 is a flowchart showing color tone correction processing in the third embodiment.

In the third embodiment, processing operations for the two LUTs may be executed separately from each other. That is, among the processing steps shown in FIGS. 19 and 20, the processing portion shown in FIG. 20 may be executed for each LUT separately at S66 and S67, as shown in FIG. 22. The processing shown in FIG. 21 may be replaced by processing as shown in FIG. 23. That is, conversion or calculation of the pixel value may be executed for each LUT separately at S75 and S76. The processing sequence may be reversed.

Although in the third embodiment the memory 136 having LUT is provided for each endoscope 1, the arrangement may be such that a plurality of memories 136 are disposed in the light source apparatus 10, and a LUT for correction of color tone variation depending on the light guide fiber bundle 4 is selected according to the type of endoscope 1 connected to the light source apparatus 10. Selection of a LUT may be automatically made on the basis of an identification signal from the endoscope 1. It is also possible to arrange the system so that the user selects a suitable LUT.

Figure 24:
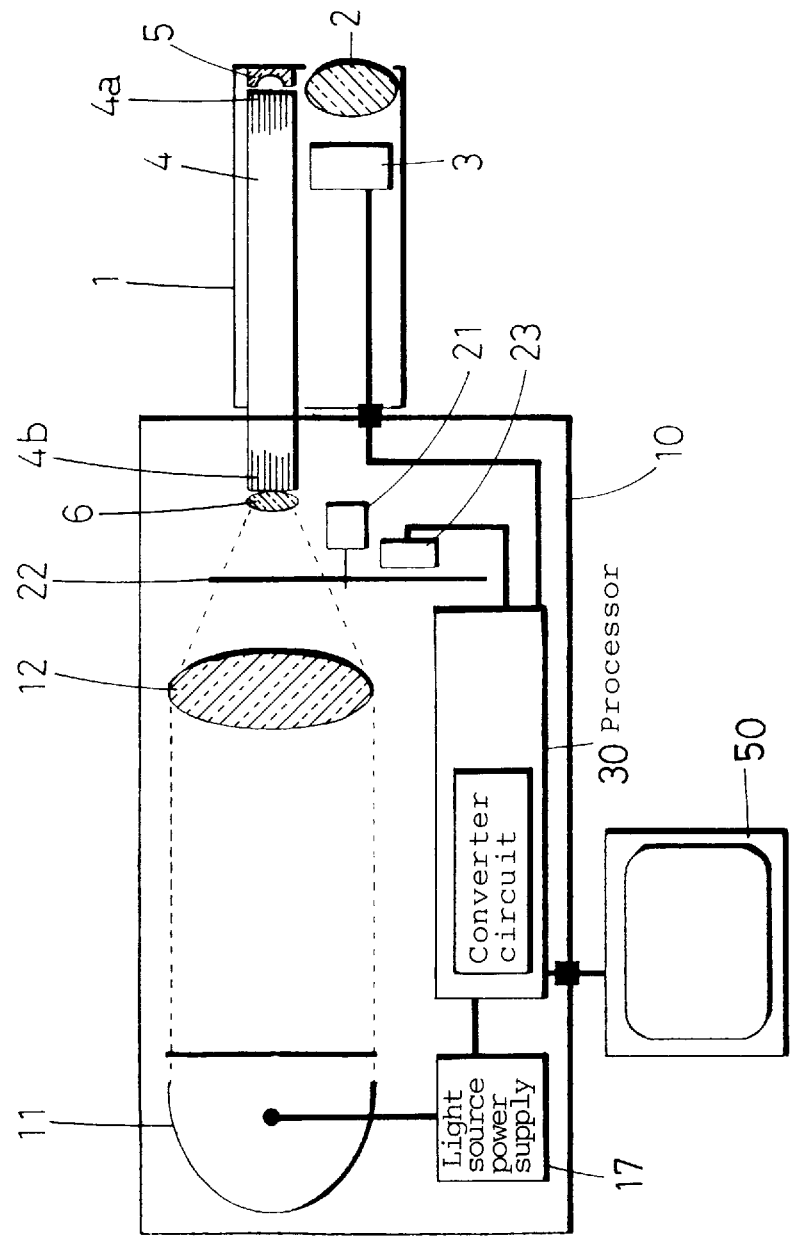
FIG. 24 schematically shows the arrangement of a video endoscope system according to a fourth embodiment of the present invention.
Figure 25:
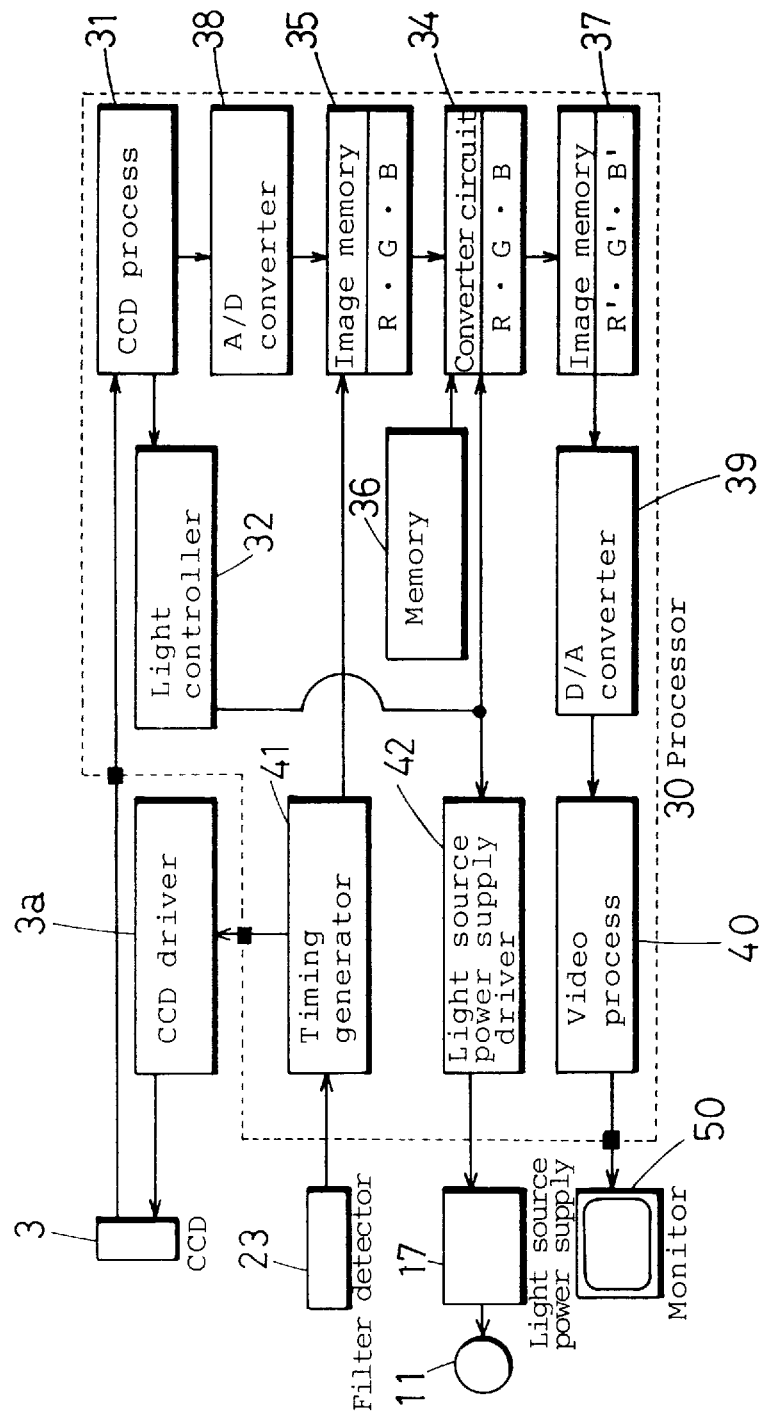
FIG. 25 schematically shows the arrangement of a processor and peripheral units attached thereto in the fourth embodiment.

FIGS. 24 and 25 show the arrangement of a fourth embodiment of the present invention, in which the luminous flux (brightness) of illuminating light emitted from the endoscope 1 and entering the light guide fiber bundle 4 is controlled by varying the voltage applied to the light source lamp 11 from a light source power supply 17 and thus changing the brightness of light emitted from the light source lamp 11.

Accordingly, the movable diaphragm 13 and the motor 16 for rotating it are not provided in this embodiment. Instead, a control signal for varying the voltage applied to the light source lamp 11 from the light source power supply 17 is output to the light source power supply 17 from a light source power supply driver 42 provided in the processor 30.

The arrangement of the rest of the fourth embodiment is the same as that of the first embodiment. In this embodiment also, LUTs (Look-Up Tables) similar to those shown in FIGS. 5 and 6 may be used for color tone correction. In the tables used in the fourth embodiment, however, the light source voltage is used in place of the diaphragm angle.

Figure 26:
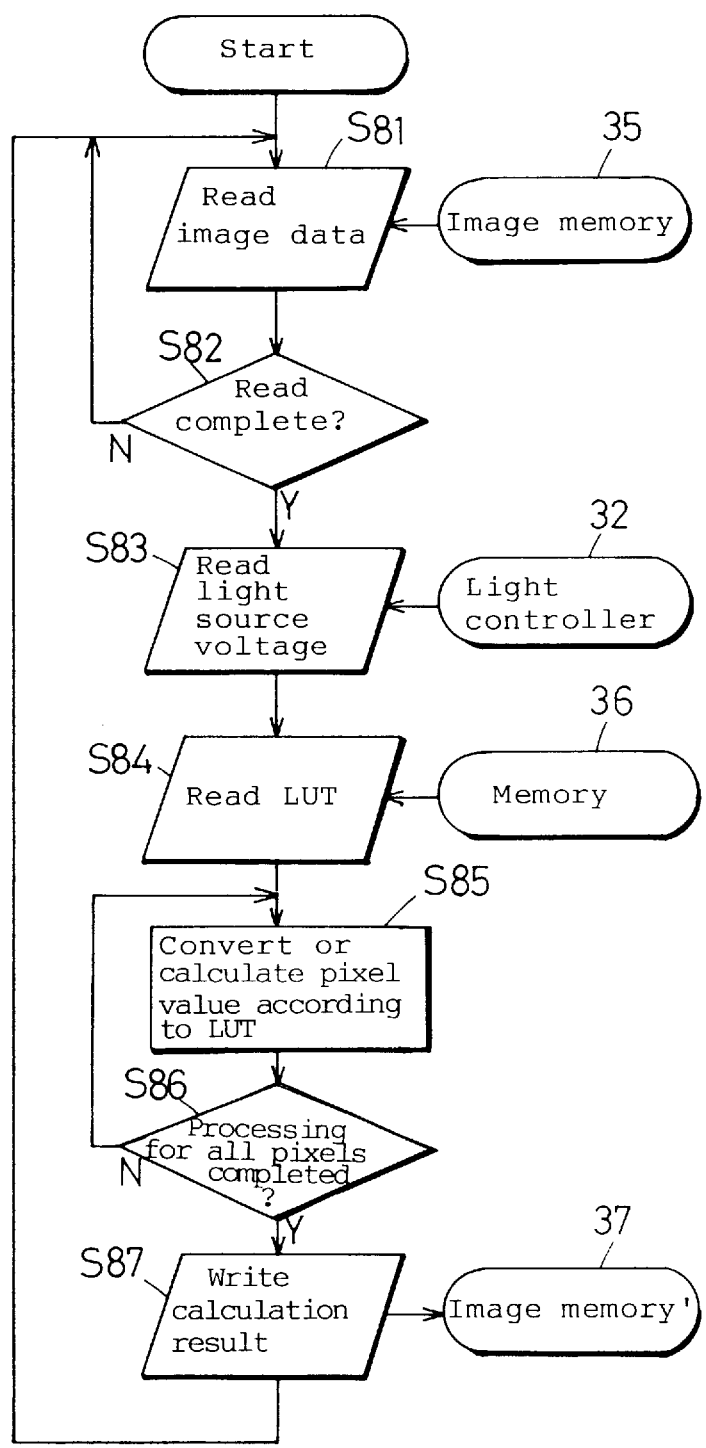
FIG. 26 is a flowchart showing color tone correction processing in the fourth embodiment.

The control processing executed by the processor 30 in the fourth embodiment is the same as the control processing in the first embodiment shown in FIG. 7 except that, in this embodiment, conversion data corresponding to the voltage applied to the light source lamp 11 from the light source power supply 17 is read from the light controller circuit 32 (S83), as shown in FIG. 26, whereas, at S3 in FIG. 7, diaphragm angle data is read from the light controller circuit 32.

It should be noted that the color conversion information recorded in the LUTs stored in the memories 36 and 136 in the above-described embodiments are installed so that these data can be rewritten by performing calibration when maintenance is carried out, or on other occasions.

Further, the light source apparatus 10 adapted to have color conversion information corresponding to various types of endoscope should be arranged such that LUT data can be additionally written when a new endoscope is developed.

According to the present invention, an endoscope image that is output from a solid-state imaging device and processed in a processor is divided into a plurality of regions, and color tone correction is made with respect to each region of the image according to the control condition of a device for controlling the luminous flux of illuminating light supplied to a light guide. Accordingly, favorable color reproducibility can be obtained throughout the endoscope image independently of the change in control condition of the luminous flux control device.

Further, since color tone correction can be flexibly made according to the type of endoscope used, favorable color reproducibility can be obtained throughout the endoscope image independently of the type of endoscope used.

While the invention has been described by reference to specific embodiments chosen for purposes of illustration, it should be apparent that numerous modifications could be made thereto by those skilled in the art without departing from the basic concept and scope of the invention.

We claim:

1. A video endoscope system comprising:

luminous flux controlling means for emitting illuminating light rays of at least three colors sequentially by color, and for controlling a luminous flux of each of said illuminating light rays;

a light guide for transmitting said illuminating light rays from said luminous flux control means to illuminate an observation field of an endoscope;

a solid-state imaging device for taking endoscope images of an object illuminated by said illuminating light rays sequentially by color, and for outputting sequentially by color a plurality of signals representing single color images, each of said single color image signals corresponding to one of said at least three colors; and a processor for combining said single color image signals into one composite full-color image of said object, said processor dividing each of said single color images into a plurality of predetermined regions, and said processor making color tone correction by correcting an intensity of each predetermined region of each of said single color images according to color conversion data depending on said control of said luminous flux controlling means.

2. A video endoscope system comprising:

a light source for emitting illuminating light;

a luminous flux regulating system for regulating a luminous flux of said illuminating light by predetermined steps;

a separating device for separating said illuminating light into at least three different colors;

a light guide for transmitting said at least three different colors of said illuminating light to illuminate an observation field of an endoscope;

a solid-state imaging device for receiving different color images of said observation field, each of said different color images being divided into predetermined regions and each of said different color images corresponding to one of said at least three different colors;

means for calculating color conversion data in accordance with said predetermined steps of said luminous flux regulating system and with image input levels of each predetermined region of each different color image of said observation field; and a processor for correcting an intensity of each predetermined region of each of said different color images according to said color conversion data, and for combining said different color images into a corrected composite full-color image of said object.

3. The video endoscope system according to claim 2, wherein said color conversion data is color tone correction data, and said processor corrects color tone of each predetermined region of each of said different color images according to said color tone correction data.

4. The video endoscope system according to claim 3, each of said concentric regions being a concentric circular region.

5. The video endoscope system according to claim 3, each of said concentric regions being a concentric polygonal region.

6. The video endoscope system according to claim 3, each of said predetermined regions being a unit pixel region, and said processor correcting color tone by correcting an intensity of each unit pixel region of each of said different color images.

7. A video endoscope system comprising:

a light source for emitting illuminating light;

a mechanism for controlling a luminous flux of said illuminating light;

device for sequentially separating said illuminating light into at least three colors;

a light guide for transmitting said at least three colors of said illuminating light to illuminate an observation field of an endoscope;

a solid-state imaging device for receiving endoscope images of an object illuminated by said at least three colors of illuminating light, and for sequentially outputting single color images;

a processing device for dividing each of said single color images into a plurality of predetermined regions;

a color tone correction device for correcting, by predetermined region, an intensity of each predetermined region of each of said single color images;

a processor for combining said corrected single color images into a corrected composite full-color image of said object.

8. The video endoscope system according to claim 3, each of said predetermined regions being a concentric region, and said processor correcting color tone by correcting an intensity of each concentric region of each of said different color images.

9. The video endoscope system according to claim 2, said luminous flux regulating system comprising an aperture diaphragm for changing a cross-sectional area of said luminous flux of said illuminating light to regulate said luminous flux before said illuminating light enters said light guide.

10. The video endoscope according to claim 2, wherein said aperture diaphragm comprises a set of parallel flat plates within said luminous flux rotatable from a position parallel to an optical axis of said illuminating light source.

11. The video endoscope according to claim 2, wherein said luminous flux regulating system comprises a light source driving circuit capable of varying a voltage applied to said light source to change an output of luminous flux of said light source.

12. The video endoscope system according to claim 2, wherein said means for calculating color conversion data comprises a memory containing a plurality of look-up tables corresponding to said predetermined regions of each different color image of said observation field, each look-up table containing color conversion data corresponding to each of said predetermined steps of said light regulating system.

13. The video endoscope system according to claim 12, wherein said look-up tables contain color conversion data corresponding to predetermined regions of red, green, and blue different color images of said observation field.

14. The video endoscope system according to claim 2, further comprising means for further calculating color conversion data in accordance with optical characteristics of said endoscope, including optical characteristics of said light guide.

15. The video endoscope system according to claim 14, wherein said means for calculating color conversion data comprises a first memory containing a plurality of look-up tables containing color conversion data corresponding to said predetermined steps of said light regulating system, and wherein said means for further calculating color conversion data comprises a second memory containing at least one look-up table containing color conversion data corresponding to said optical characteristics of said light guide.

16. The video endoscope system according to claim 2, said separating device comprising color filters for separating said illuminating light from said light source into said at least three different colors.

17. A video endoscope system according to claim 15, wherein said light guide and said solid-state imaging device are incorporated in said endoscope, while said light source and said processor are incorporated in a light source apparatus that is separate from said endoscope, said first memory being disposed in said light source apparatus, and said second memory being disposed in said endoscope.

18. A video endoscope system according to claim 15, wherein said light guide and said solid-state imaging device are incorporated in said endoscope, while said light source and said processor are incorporated in a light source apparatus that is separate from said endoscope, said first memory and said second memory being disposed in said light source apparatus.

19. A video endoscope system comprising:

a light source for emitting illuminating light;

a light regulating system for regulating a luminous flux of said illuminating light by predetermined steps;

a separating device for separating said illuminating light into at least three different colors;

a light guide for transmitting said at least three different colors of said illuminating light to illuminate an observation field of an endoscope;

a solid-state imaging device for receiving different color images of said observation field, each of said different color images being divided into predetermined regions and each of said different color images corresponding to one of said at least three different colors;

a memory containing a plurality of look-up tables corresponding to said predetermined regions of each different color image of said observation field, each look-up table containing color conversion data corresponding to each of said predetermined steps of said light regulating system; and a processor for correcting, by said predetermined regions, an intensity of each predetermined region of each of said different color images according to said color conversion data, and for combining said different color images into a corrected composite full-color image of said object.

20. A video endoscope system comprising:

means for emitting a luminous flux regulated by predetermined steps;

means for separating said luminous flux into at least three different colors;

a light guide for transmitting said at least three different colors of said illuminating light to illuminate an observation field of an endoscope;

means for receiving different color images of said observation field, each of said different color images being divided into predetermined regions and each of said different color images corresponding to one of said at least three different colors;

means for calculating color conversion data corresponding to each of said predetermined steps of said light regulating system in accordance with an input level of each predetermined region of each different color image of said observation field;

means for correcting, by said predetermined regions, an intensity of each predetermined region of each of said different color images according to said color conversion data; and means for combining said different color images into a corrected composite full-color image of said object.

21. A video endoscope system comprising:

a light source for emitting illuminating light;

a light regulating system for regulating a luminous flux of said illuminating light by predetermined steps;

a separating device for separating said illuminating light into at least three different colors;

a light guide for transmitting said at least three different color images of said observation light to illuminate an observation field of an endoscope;

a solid-state imaging device for receiving different color images of said observation field, each of said different color images being divided into predetermined regions and each of said different color images corresponding to one of said at least three different colors;

a memory containing a plurality of look-up table corresponding to said predetermined steps of said light regulating system, each look-up table containing color conversion data corresponding to each of said different color images of said observation field; and a processor for correcting, by said predetermined regions, an intensity of each predetermined region of each of said different color images according to said color conversion data, and for combining said different color images into a corrected composite full-color image of said object.

22. A video endoscope system comprising: means for emitting a luminous flux regulated by predetermined steps;

means for separating said luminous flux into at least three different colors;

a light guide for transmitting said at least three different colors of said illuminating light to illuminate an observation field of an endoscope;

means for receiving different color images of said observation field, each of said different color images being divided into predetermined regions and each of said different color images corresponding to one of said at least three different colors;

means for calculating color conversion data corresponding to each predetermined region of each different color image of said observation field based on each of said predetermined steps of said light regulating system;

means for correcting, by said predetermined regions, an intensity of each predetermined region of each of said different color images according to said color conversion data; and means for combining said different color images into a corrected composite full-color image of said object.

* * * * *

UNITED STATES PATENT AND TRADEMARK OFFICE
CERTIFICATE OF CORRECTION

PATENT NO. : 5,864,361
DATED : January 26, 1999
INVENTOR(S) : T. SEKIYA, ET AL.

It is certified that error appears in the above-identified patent and that said Letters Patent is hereby corrected as shown below:

At line 37  On the title page:Item [56]  change "Lnaguage" to —Language—.

At column 12, line 8 (claim 21, line 8), change "color images of said observation" to —colors of said illuminating—.

At column 12, line 17 (claim 21, line 15) change "table" to —tables—.

Signed and Sealed this

Seventh Day of December, 1999

Attest:

Q. TODD DICKINSON

*Attesting Officer*  *Acting Commissioner of Patents and Trademarks*